(12) United States Patent
Schroeder et al.

(10) Patent No.: US 7,282,213 B2
(45) Date of Patent: Oct. 16, 2007

(54) METHOD FOR APPLYING A DRUG COATING TO A MEDICAL DEVICE

(75) Inventors: Peter T. Schroeder, Minneapolis, MN (US); Kimberly A. Chaffin, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 514 days.

(21) Appl. No.: 10/260,659

(22) Filed: Sep. 30, 2002

(65) Prior Publication Data

US 2004/0062852 A1  Apr. 1, 2004

(51) Int. Cl.
*A61F 13/00* (2006.01)
*A61N 1/00* (2006.01)

(52) U.S. Cl. .............. 424/422; 424/425; 424/426; 607/115; 607/116; 607/120

(58) Field of Classification Search ........ 424/422–426; 607/115, 116, 120
See application file for complete search history.

(56) References Cited

U.S. PATENT DOCUMENTS

| | | | |
|---|---|---|---|
| 3,886,103 A * | 5/1975 | Koizumi et al. ............ 524/104 |
| 4,502,492 A | 3/1985 | Bornzin | |
| 4,506,680 A | 3/1985 | Stokes | |
| 4,577,642 A | 3/1986 | Stokes | |
| 4,606,118 A | 8/1986 | Cannon et al. | |
| 4,953,564 A | 9/1990 | Berthelsen | |
| 5,324,325 A | 6/1994 | Moaddeb | |
| 5,522,874 A | 6/1996 | Gates | |
| 5,658,327 A | 8/1997 | Altman et al. | |
| 5,776,178 A | 7/1998 | Pohndorf et al. | |
| 5,837,007 A | 11/1998 | Altman et al. | |
| 5,987,746 A * | 11/1999 | Williams ................. 29/876 |
| 2002/0077685 A1 | 6/2002 | Sundquist et al. .......... 607/116 |

FOREIGN PATENT DOCUMENTS

| EP | 0 414 233 | | 2/1991 |
|---|---|---|---|
| EP | 0 414 233 B1 | * | 10/1996 |
| WO | WO99/53994 | | 10/1999 |

* cited by examiner

*Primary Examiner*—Michael G. Hartley
*Assistant Examiner*—Micah-Paul Young
(74) *Attorney, Agent, or Firm*—Girma Wolde-Michael; Michael C. Soldner; Carol F. Barry

(57) ABSTRACT

A method for coating a medical device with a drug is provided. Energy, preferably thermal energy, is applied to a crystalline deposit of a drug on the surface of a medical device to increase the molecular mobility and form a conformable drug coating with a low density of micro-cracks and other mechanical defects that can degrade the coating toughness and effective adhesion to the device surface. In a preferred embodiment, solution evaporation methods are used to deposit a crystalline coating of an anti-inflammatory steroid on a medical electrode. Heat applied at a controlled temperature, for a predetermined amount of time, induces a solid-state phase change of the drug coating providing a smooth, uniform, well-attached, conformable coating to form a layer that will elute from the electrode over time when implanted in a patient's body.

27 Claims, 4 Drawing Sheets

METHOD FOR APPLYING A DRUG COATING TO A MEDICAL DEVICE

FIELD OF THE INVENTION

The present invention relates to implantable medical devices and, more specifically, to a method for coating a medical device, such as a medical electrode, a stent, or other implantable device, with a pharmaceutical agent.

BACKGROUND OF THE INVENTION

Electrical stimulation of excitable body tissue is used as a method of treating various pathological conditions. Such stimulation generally entails making an electrical contact between excitable tissue and an electrical pulse generator through use of one or more stimulation leads. Various lead systems and various techniques for implanting these lead systems in contact with excitable body tissue, and particularly the heart, have been developed.

In order to achieve cardiac pacing, sensing, cardioversion and/or defibrillation, various types of cardiac leads have been developed including epicardial leads, endocardial leads, and coronary sinus leads. For example, a transvenous endocardial lead establishes electrical contact between an electrical pulse generator, such as a pacemaker or implantable cardioverter defibrillator, and a patient's heart through placement of the lead in the venous system. Specifically, a transvenous endocardial lead is passed through a vein, with the assistance of a fluoroscope, into the heart where it may be held in contact with the endocardium by the trabeculae of the heart chamber, such as the ventricle. The safety, efficacy and longevity of an electrical pulse generator depends, in part, on the performance of the associated cardiac lead(s) used in conjunction with the pulse generator.

For example, various properties of the lead and electrodes will result in a characteristic impedance and stimulation threshold. Stimulation threshold is the energy required in a stimulation pulse to depolarize, or "capture," the heart tissue. A relatively high impedance and low threshold is desired to minimize the current drawn from a pulse generator battery in delivering a stimulation pulse. Maximizing the useful life of the pulse generator battery is important battery has reached the end of its useful life.

One factor that can affect the stimulation threshold, particularly during the first several weeks after implantation of a lead, is the natural immunological response of the body to the lead as a foreign object. The presence of the lead activates macrophages, which attach themselves to the surface of the lead and any electrodes and form multi-nucleated giant cells. These cells, in turn, secrete various substances, such as hydrogen peroxide as well as various enzymes, in an effort to dissolve the foreign object. Such substances, while intending to dissolve the foreign object, also inflict damage to the surrounding tissue. When the surrounding tissue is the myocardium, these substance cause necrosis. These areas of necrosis, in turn, impair the electrical characteristics of the electrode-tissue interface. Consequently pacing thresholds rise. Even after the microscopic areas of tissue die the inflammatory response continues and approximately seven days after implant the multi-nucleated giant cells cause fibroblasts to begin laying down collagen to replace the necrotic myocardium. Eventually, on the order of three weeks after implant, the lead and its electrodes are encapsulated by a thick layer of fibrotic tissue. Typically the inflammatory response ends at this time. The fibrotic encapsulation of the lead and its electrodes, however, remains. Since the fibrotic tissue is not excitable tissue, an elevated stimulation threshold can persist due to the degraded electrical properties of the electrode-tissue interface.

A considerable breakthrough in the development of low threshold electrode technology occurred with the invention of the steroid eluting porous pacing electrode of Stokes U.S. Pat. No. 4,506,680 and related Medtronic U.S. Pat. Nos. 4,577,642, and 4,606,118. Steroid, it is believed, inhibits the inflammatory response by inhibiting the activation of the macrophages. Because they do not form multi-nucleated giant cells, the subsequent release of substances to dissolve the object and which also destroy the surrounding tissue is prevented. Thus the necrosis of any tissue by the inflammatory response is minimized as well as the formation of the fibrotic capsule. Minimizing each of these reactions also minimizes the concomitant deterioration of the electrical characteristics of the electrode-tissue interface. The electrode disclosed in the '680 patent was constructed of porous, sintered platinum or titanium, although carbon and ceramic compositions were mentioned. Within the electrode, a plug of silicone rubber impregnated with the sodium salt of dexamethasone phosphate or a water soluble form of another glucocorticosteroid was placed in a chamber. The silicone rubber plug allowed the release of the steroid through the interstitial gaps in the porous sintered metal electrode to reach into the tissue and prevent or reduce inflammation, irritability and subsequent excess fibrosis of the tissue adjacent to the electrode itself.

Thus, the incorporation of steroid elution permitted pacing leads to have a source impedance substantially lower as compared to leads featuring similarly sized solid electrodes. Leads which elute steroid also presented significantly lower peak and chronic pacing thresholds than similarly sized solid or porous electrodes. One example of a lead which eluted steroid meeting widespread commercial success is the Medtronic Model 5534 CAPSURE Z™ lead. The electrode was fabricated of platinized porous platinum and equipped with an annular shaped monolithic controlled release device (MCRD) loaded with an anti-inflammatory agent soluble in water, e.g. the steroid dexamethasone sodium phosphate. The steroid would elute out of the lead and into the surrounding tissue. This water soluble steroid also was deposited within the pores of the porous platinum electrode.

Incorporating steroid so that it will elute from a lead, however, increased the complexity of lead construction as compared to past, non-steroid eluting leads. For example, leads which elute steroid typically require an MCRD to contain the steroid and to thereafter slowly leach out the water soluble steroid into the surrounding tissue. Typically MCRDs were constructed from silicone rubber. Steroid eluting leads also required an area near the electrode in which to house the MCRD, as well as a high degree of dimensional control over the electrode in order to ensure proper steroid elution. Setting aside a volume near the electrode tip to house the MCRD, however, also tended to increase lead body stiffness in that area. The MCRD typically swells over time as the drug elutes from the polymer structure and is replaced by water and electrolytes.

Since the area of greatest concern for minimizing the immunologic response and fibrotic encapsulation is at the electrode itself, it would be desirable to provide a steroid-eluting electrode having steroid released directly at the electrode-tissue interface. One method for applying a steroid to the surface of an electrode is disclosed in U.S. Pat. No. 5,987,746 to Williams, incorporated herein by reference in its entirety. In this method, a solution mixed from an organic solvent and a steroid that is no more than sparingly soluble in water is applied to a lead. The solution is dried to drive of the organic solvent. The remaining steroid, because it is no more than sparingly soluble in water, will not quickly dissolve away from the electrode surface once in contact with bodily fluids and will remain at the electrode-tissue interface long enough to have a desired pharmacological effect. Advantages of this method include elimination of additional structures for carrying the steroid and the presentation of the steroid directly at the tissue-electrode interface.

One limitation of applying a steroid in solution to an electrode, however, is that the steroid remaining on the electrode surface after the solvent has evaporated generally forms a crystalline coating. The surface morphology of this crystalline coating is generally rough, where the roughness is a function of the crystal growth rate and crystal orientation. When two adjacent crystals impinge, further growth is suppressed. A micro-crack can form at the crystal-crystal boundary due to slight orientational mis-alignment of the crystals. These micro-cracks often propagate under small loads. Upon exposure to fluids, capillary forces cause fluid to enter the micro-cracks. Forces imparted by the fluid within the micro-cracks cause the cracks to dilate and grow in length, resulting in mechanical deterioration of the coating. Thus, a solution-deposited drug coating is generally not well adhered to the electrode surface and may easily flake or brush away during handling of the lead for manufacturing and implant procedures. The amount of steroid remaining on the electrode surface once delivered to an implant site may, therefore, be uncertain. It would be desirable to provide an electrode with a steroid coating that is durable enough to remain well-attached to the electrode surface during lead handling and still have the advantages of steroid elution directly at the electrode-tissue interface with elimination of additional structures required for carrying the steroid.

SUMMARY OF THE INVENTION

The present invention provides an improved method for applying a drug coating to an implantable medical device, such as an electrode. The method generally includes depositing a drug on a medical device surface, heating the drug to cause a phase change and healing of micro-cracks, and allowing the drug to cool such that it forms a crystalline coating that is better conformed to the electrode surface.

In a preferred embodiment, a saturated solution is prepared by dissolving an anti-inflammatory steroid in an organic solvent. The drug solution is dispensed onto a medical electrode. The solvent is allowed to evaporate leaving a crystalline coating of the steroid on the electrode surface. Heat is then applied to the crystalline coating to increase the molecular mobility causing a reorganization of the crystalline structure resulting in micro-crack healing and producing a conformable coating. Focused, localized heat is preferably applied to the crystalline coating at a controlled temperature for a controlled amount of time such that the coating is quickly heated to a point that causes a solid-state phase change and micro-crack healing without degrading the drug. During the solid-state phase change, the drug flows over the electrode surface and, upon cooling, forms a uniform, smooth, conformable coating.

The methods included in the present invention allow a drug coating to be applied to an electrode surface in which the amount of drug deposited and the resulting surface morphology are controlled and reproducible. The conformable crystalline coating is well attached and more durable than the rougher crystalline coating obtained prior to heating because the thermal processing has significantly reduced the defect density of the drug coating. Reorganization of the crystalline structure during thermal processing is thus expected to increase the durability of the coating in at least two ways. First, the surface area in direct contact with the electrode surface may be increased as the coating conforms to the electrode surface, resulting in an apparent increase in adhesion. Second, the cohesive strength of the drug coating may be improved through the elimination of defects. The drug-coated electrode is therefore expected to have improved manufacturability and handling properties after thermal processing. Because the coating is less likely to break or flake away during manufacturing and implant, greater confidence is achieved in providing a known amount of drug at an electrode- or device-tissue interface.

DETAILED DESCRIPTION OF THE INVENTION

The present invention is aimed at providing a medical electrical lead having a drug-coated electrode surface and a method for manufacture that allows the amount of drug present and the resulting surface morphology of the drug coating to be controlled and reproducible.

The inventor has found that under controlled conditions, a drug coating applied to an electrode surface of a medical lead may be heated to induce a solid-state phase change that results in micro-crack healing of the inter-crystalline grain boundaries and a transition from an opaque, relatively fragile coating to a translucent, conformable coating, without degradation of the drug. Thermally induced re-organization of the crystalline structure produces a conformable coating that has a much lower defect density than its precursor, and consequently yields higher effective adhesion and durability than the coating that was deposited from solution. Prior attempts at heating a drug coating to create a smooth, more durable, surface coating on an electrode have been less successful due to chemical decomposition of the drug. Certain attempts at heating a drug coating on an electrode surface, including heating a drug-coated electrode in an oven or applying hot forceps to a drug-coated electrode, either resulted in drug degradation or incomplete phase change and reorganization of the crystalline structure. The defect density was not significantly reduced, producing inconsistent results with a coating that was generally bubbled and opaque in appearance. The methods that will be described herein advantageously provide a steroid-coated electrode having a coating that is smooth, uniform, and well-attached to the electrode surface.

Figure 1:
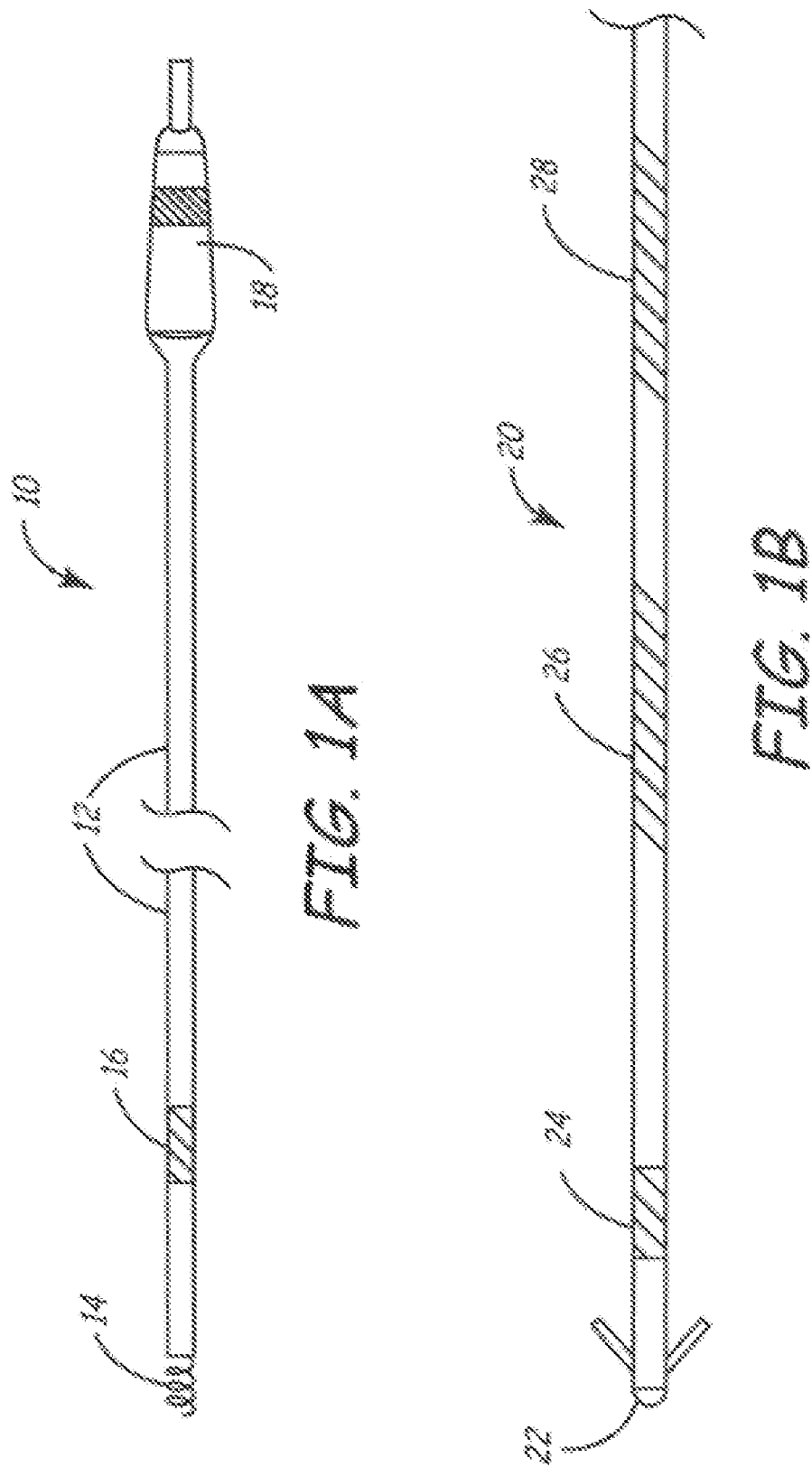
FIG. 1A is a plan view of a cardiac pacing lead that may be used in conjunction with the present invention.
FIG. 1B is a plan view of the distal end of a cardiac pacing and defibrillation lead that may be used in conjunction with the present invention.

FIGS. 1A and 1B depict exemplary medical leads of the type that may be used with the present invention. FIG. 1A is a plan view of a medical lead 10 that may typically be used for cardiac pacing and/or sensing. Lead 10 is provided with an elongated lead body 12, a helical tip electrode 14 located at the distal end of the lead and a ring electrode 16 spaced proximally from tip electrode 14. A connector assembly 18 at the proximal end of lead 10 is used to connect the lead to a medical device, such as a pacemaker. Conductors extending the length of lead body 12 electrically couple the tip electrode 14 and ring electrode 16 to respective connectors carried by the connector assembly 18.

FIG. 1B is a plan view of the distal end of a medical lead 20 of the type that may be used for pacing, sensing, cardioversion and/or defibrillation. Lead 20 is provided with a tip electrode 22 and a ring electrode 24, which are generally used for pacing and/or sensing, and two defibrillation coil electrodes 26 and 28 for delivering high-energy shocking pulses for cardioversion or defibrillation.

A medical electrode used with the present invention is preferably fabricated from a conductive biocompatible material, such as platinum, iridium, titanium or alloys thereof. The electrode surface may also be treated or coated in a way that reduces polarization effects at the electrode-tissue interface, for example as disclosed in the '680 patent or in U.S. Pat. No. 4,502,492 to Bornzin, incorporated herein by reference in its entirety.

The exemplary leads 10 and 20 of FIGS. 1A and 1B illustrate various electrode structures, including ring electrodes (16 and 24), coil electrodes (26 and 28), helical electrodes (14), or generally hemispherical electrodes (22), with which the present invention may be used. The performance of other electrodes of various geometries may also be improved when the electrode is treated according to the methods provided by the present invention for applying a drug coating to a medical device. The application of the present invention is therefore not limited to the types of electrodes depicted in FIGS. 1A and 1B. Rather, the present invention may also be used in conjunction with other types of cardiac electrodes or electrodes for neurological stimulation or sensing, smooth or skeletal muscle stimulation or sensing, or any other types of medical electrodes. Furthermore, the methods provided by the present invention may be applied to other types of implantable medical devices such as stents, prosthetic devices, implantable pulse generator housings, or any other medical device with which a drug coating is desired for providing a local pharmaceutical effect in tissue in contact with the device.

Figure 2:
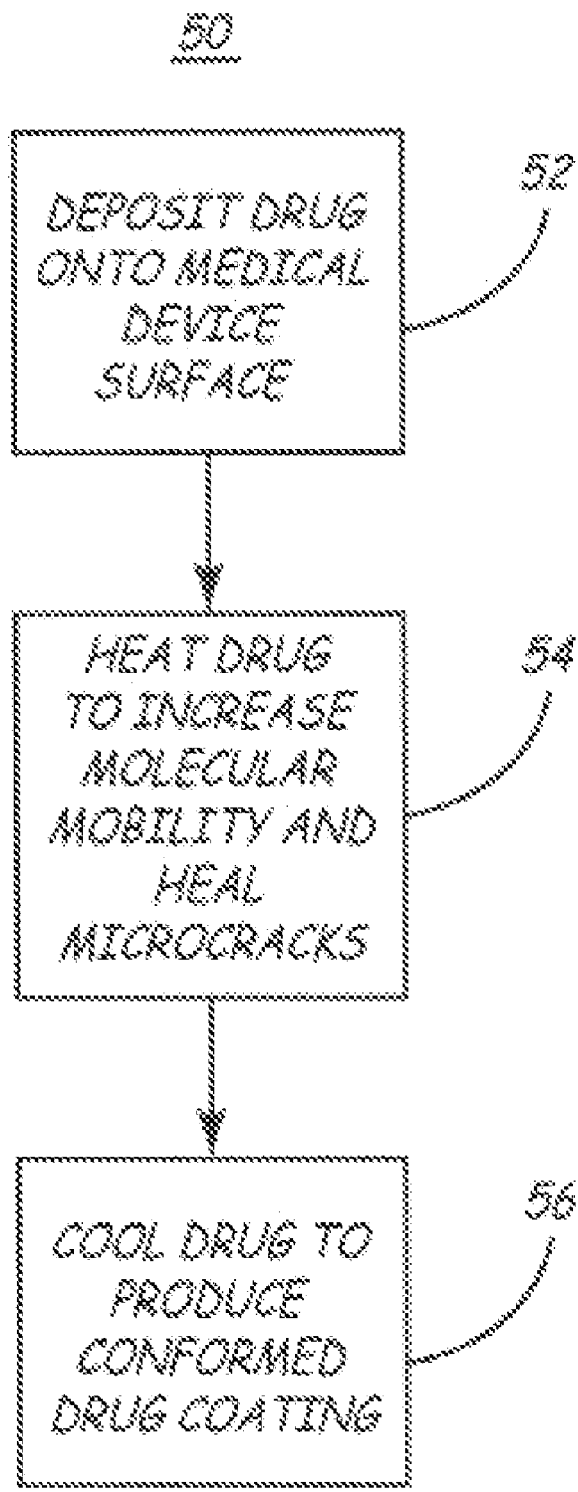
FIG. 2 is a flow chart providing an overview of the general steps included in a method for coating a medical device with a pharmaceutical agent in accordance with the present invention.

FIG. 2 is a flow chart providing an overview of the general steps included in a method for coating a medical device with a pharmaceutical agent in accordance with the present invention. The method generally includes: depositing a drug on the surface of a medical device at step 52; applying heat at step 54 to increase the molecular mobility and allow micro-crack healing of the inter-crystalline grain boundaries in the drug coating; and cooling the drug at step 56 to form a uniform, smooth drug coating that generally conforms to the device surface.

Imparting energy in the form of heat to the crystalline drug deposit increases the molecular mobility of the drug allowing reorganization of its crystalline structure, probably to a lower free energy state. Thermal processing is expected to increase the durability of the coating in at least two ways. First, the surface area in direct contact with the electrode surface may be increased as the crystalline coating conforms to the electrode surface, resulting in an apparent increase in adhesion. Second, the cohesive strength of the drug coating may be improved through the elimination of micro-cracks or other defects that normally degrade the toughness of the coating. The drug-coated electrode is therefore expected to have improved manufacturability and handling properties after thermal processing.

Alternative methods for imparting energy to a crystalline drug coating, other than heating, have been contemplated. For example, it is conceivable that radio-frequency energy or microwave energy may be applied to a deposited drug coating to produce a conformable drug coating. The type of energy selected will partly depend on the material from which the medical device is formed. Polymeric structures, for example, may withstand microwave processing to produce a conformable drug coating. However, metallic structures, such as metal electrodes, may more easily undergo thermal processing as will be described herein.

Figure 3:
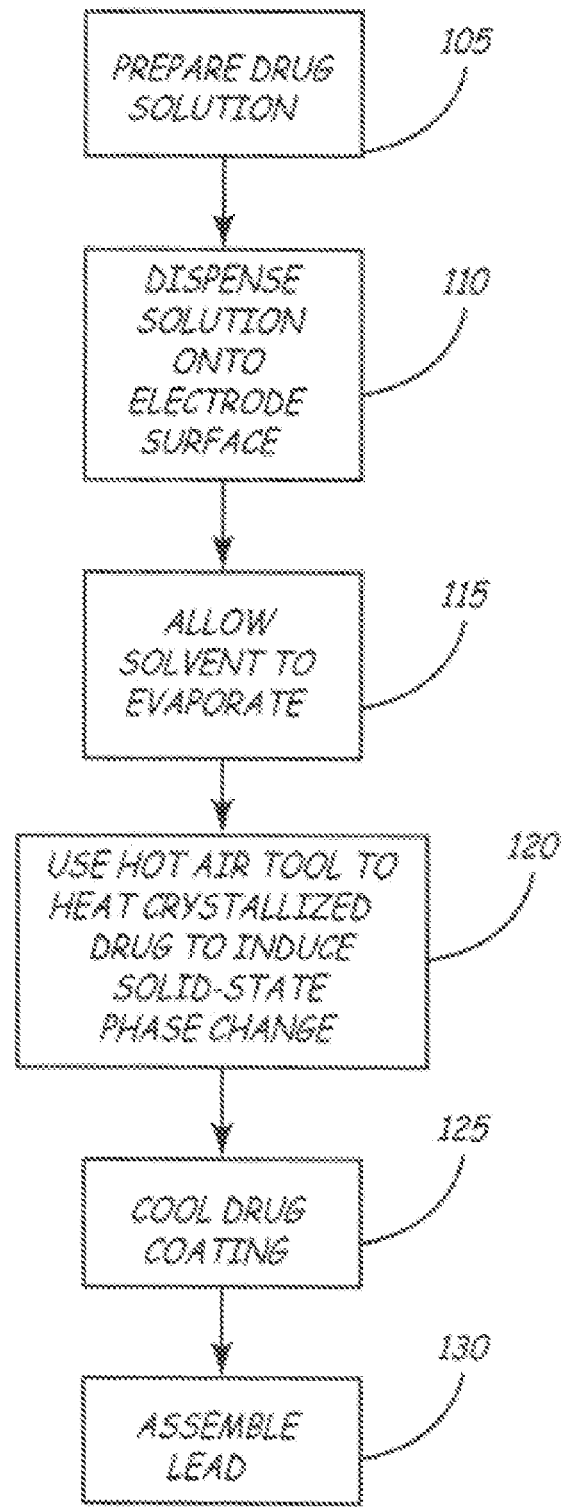
FIG. 3 is a more detailed flow chart describing the steps included in one embodiment of the method of FIG. 2 used for coating a medical electrode with a steroid.
Figure 4:
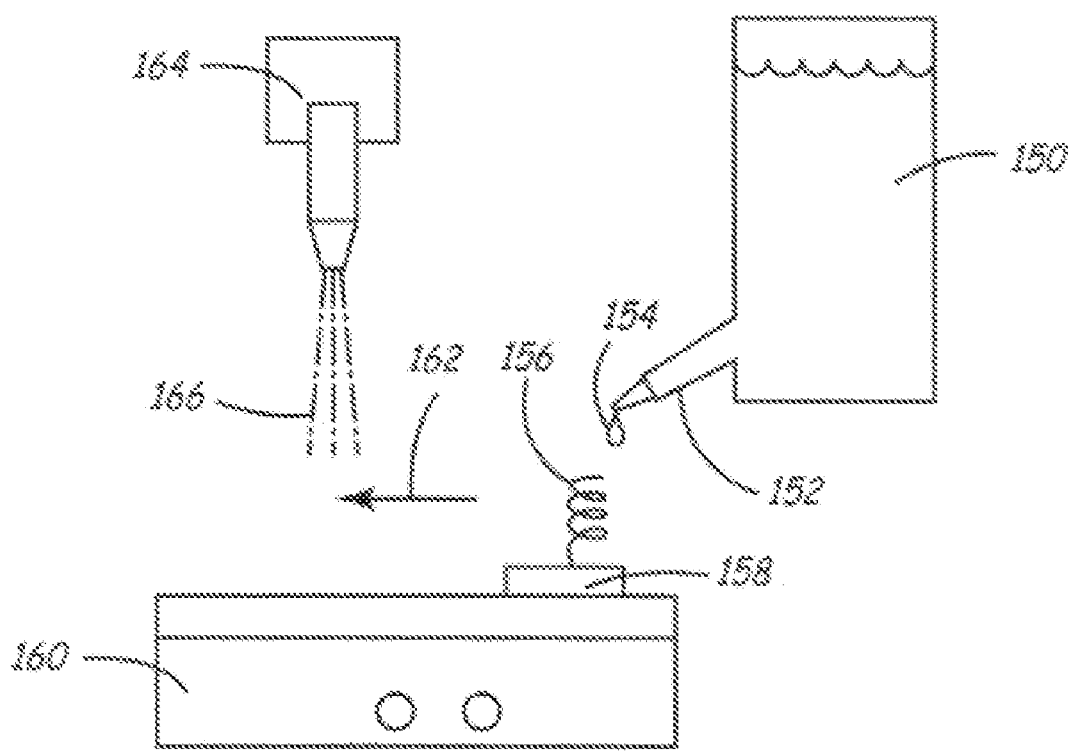
FIG. 4 is a schematic diagram of apparatus that may be used for performing the methods included in FIG. 3.

FIG. 3 is a more detailed flow chart describing the steps included in one embodiment of the method of FIG. 2, which may be used for coating a medical electrode with an anti-inflammatory steroid for preventing inflammation at the electrode implantation site. Beginning at step 105, a drug solution is prepared. The drug solution is preferably a saturated solution of a non-aqueous organic solvent and a steroid that is no more than sparingly soluble in water. One preferred steroid for use with the present invention is beclomethasone dipropionate anhydrous because it is very slightly soluble in water and will therefore not dissolve quickly away from the electrode surface once it is in contact with bodily fluids. Beclomethasone dipropionate anhydrous may be dissolved in an appropriate organic solvent such as acetone. A suitable form of beclomethasone dipropionate anhydrous may be obtained from Vinchem, Inc., 301 Main Street, Chatham, N.J., 07928. A suitable form of acetone meets American Chemical Society specifications and may be obtained from Fisher Scientific, 711 Forbes Avenue, Pittsburgh, Pa., 15219-4785. Other types of organic solvents may also be used for preparing a solution of a drug that is no more than sparingly soluble in water, such as methanol or chloroform.

Other steroids may be used with the present invention such as betamethasone benzoate, halcinonide, diflorasone diacetate, dexamethasone or dipropionate anhydrous. Furthermore, it is conceivable that other pharmaceutical agents, other than anti-inflammatory steroids, may be applied to the surface of an electrode or other medical device or device component using methods as generally described herein. A pharmaceutical agent that is no more than sparingly soluble in water is generally preferred such that the drug will elute over time, however, drugs that are more soluble in water could also conceivably be used.

Once the drug solution is prepared, it is dispensed onto an electrode surface at step 110. A controlled amount of solution, preferably on the order of 1 to 2 microliters, is dispensed onto the electrode surface, either manually or automatically, using a syringe or other appropriate device. The amount of solution dispensed onto the electrode should sufficiently coat the electrode without significant run-off. At step 115, the solution is allowed to dry such that the solvent evaporates away from the electrode surface and the remaining drug crystallizes on the electrode surface. The drying procedure may be performed at room temperature and generally requires several minutes. At this point, the crystalline coating, like prior art methods, may produce a generally rough, loosely attached coating.

A method for applying a steroid solution to an electrode may be performed as generally described in the '746 patent. In alternative embodiments, the drug may be deposited onto an electrode surface using methods other than the solution evaporation methods described above. For example, a suspension may be prepared using a generally low solubility drug suspended in a liquid medium. After dispensing the suspension onto an electrode surface, the liquid medium may be driven off through passive evaporation or other methods leaving a deposition of the drug on the electrode surface.

A drug suspension or solution may alternatively be dip-coated onto an electrode surface and allowed to dry. A drug suspension or solution may also be applied to an electrode surface by immersing the electrode in the suspension or solution and allowing the solvent to evaporate leaving a deposit of the drug coating on the electrode surface.

A drug could alternatively be deposited to an electrode surface in a dry form. For example, a pure powdered form of the drug may be deposited on the electrode surface by dipping the electrode into the powdered drug. In one embodiment, the electrode surface may be prepared to promote adherence of the drug to the electrode surface, for example by wetting the electrode surface with an appropriate liquid medium, such as a solvent that would easily evaporate and not interfere with the pharmacological properties of the drug or the electrical properties of the electrode.

Once the drug has been deposited on the electrode surface, the drug coating is heated at step 120 to increase molecular mobility and thereby allow micro-crack healing within the crystalline structure. Preferably, the drug coating is heated to a transition point that results in a phase change, preferably a solid-state phase change. The increased molecular mobility allows the crystalline structure to reorganize, probably to a lower free energy state, producing a crystalline coating that is conformable to the electrode surface.

Heating of the crystalline coating is preferably achieved using a focused heat source that allows the coating to be heated relatively quickly, e.g. within several seconds and, more preferably within approximately one second or less, at a moderately high temperature that is below a temperature at which the drug will degrade. In a preferred embodiment, heating is performed using a heating device, such as a hot air tool, that allows heat to be applied directly to the drug coating at a controlled temperature for a controlled amount of time. The temperature of the applied heat is preferably high enough to increase the molecular mobility to a point that induces a phase change, causing a significant decrease in the defect density of the drug coating.

An effective temperature may be below the melting point, at a point that induces a solid-state phase change. Differential scanning calorimetry may be performed to determine the thermal properties of a pharmaceutical agent of interest and aid in selecting a processing temperature. The melting point of beclomethasone dipropionate, for example, is specified as 205 to 210 degrees Celsius. Degradation of the drug occurs at temperatures just slightly greater than the melting point. A solid-state phase change, which results in a transformation from a white powder to a clear form of the drug, occurs between 144 and 146 degrees Celsius. In experiments performed by the inventor, applied heat of 145 degrees Celsius using a hot air tool induced a solid-state phase change and micro-crack healing of a crystalline coating of beclomethasone dipropionate on an electrode surface. Complete melting of the drug is therefore not necessary to produce a conformable coating and could result in a loss of the drug if the liquefied drug flows off the electrode surface. Depending on the properties of the drug used, if the heating temperature is not tightly controlled, the drug may degrade. Heating to the point of a solid-state phase change, therefore, advantageously reduces the risk of drug degradation, prevents the loss of drug due to run-off, and requires less heat to perform the thermal processing. Heating to a temperature equal to or greater than the solid-state transition point but less than the degradation temperature produces an increase in molecular mobility that allows effective micro-crack healing and defect reduction without drug degradation.

In addition to controlling the temperature applied to heat the crystalline coating, the total heating time is also preferably controlled. Heat may be applied for a controlled amount of time by either removing the heat source or withdrawing the electrode from the heat source once the rough, crystalline coating is changed to a conformable, crystalline coating.

Upon heating, the drug coating will flow over the surface of the electrode as the molecular mobility is increased. In the particular drug used in the example, a solid-state phase change assisted in providing a lower free energy state that drove an increase in molecular mobility as the transition occurred. The high-energy state micro-cracks healed during the solid-to-solid state transition. The result was that that the drug coating that was white and fragile turned into a translucent, conformable crystalline coating.

The heated coating is then allowed to cool at step 125 such that a translucent, conformable drug coating uniformly covers the electrode. The coated electrode may be cooled at room temperature, and is preferably cooled under a vacuum. The electrode, now coated with a steroid, may be used in assembling a lead at step 130, such as lead 10 or 20 shown in FIG. 1A or 1B, respectively. Because the conformable coating achieved by the methods described herein is more durable and better attached to the electrode surface than its precursor, lead assembly may be performed after the electrode is coated with a drug.

FIG. 4 is a schematic diagram of apparatus that may be used for performing the methods included in FIG. 3. A helical electrode 156 is shown mounted in a fixture 158 designed for holding the electrode 156 upright during the coating process. A syringe 152 is loaded with a prepared drug solution 150 and dispenses a small, controlled amount 154, onto the electrode 156. The syringe may be depressed by mechanical drug dispensing equipment that is commercially available, for example the Microlab Syringe Dispenser available from Hamilton Company, Reno, Nev.

After the solvent has evaporated such that a dry crystalline coating has formed on the electrode surface, the electrode 156 and fixture 158 are moved past a narrow stream of heated air 166 on motorized platform 160 at a controlled speed in the direction shown by arrow 162. To control the heating time, the motorized platform 160 may be set at a desired speed, such that the electrode is held in the heated air stream 166 just long enough to induce the desired phase change. A hot air tool 164 generates the stream of heated air 166 at a controlled temperature, selected based on the thermal properties of the drug used. An effective selected temperature may be anywhere in the range from a temperature that induces a solid-state phase change to a temperature less than the degradation point of the drug.

Prior attempts at heating a drug to form a more durable drug coating on an electrode surface have been less successful because the drug may degrade during the heating process due to overheating. One advantage of the present invention is that the controlled heating process, using a focused, direct heat source, achieves a change in solid state and micro-crack healing forming a conformable crystalline coating with a decrease in the defect density, without degrading the drug. In order to verify that the procedures described above for inducing a solid-state phase change and micro-crack healing do not result in degradation of the drug, high performance liquid chromatography (HPLC) has been performed. Electrodes coated with beclomethasone dipropionate, according to the thermal processing methods described above and shown in FIG. 3, have been soaked in a solvent to dissolve the drug coating from the electrode surface. The resulting test solution was analyzed using HPLC and compared to HPLC results from a control sample of beclomethasone dipropionate in solution. Chromatograms of the test solution samples were identical to those of the control samples with regards to retention time of the major peak. In addition no peaks associated with degradation products were observed with the test sample.

Thus, an improved method has been described for coating medical electrodes, or other implantable medical devices, with a pharmaceutical agent. It is recognized that one knowledgeable in the art may conceive variations of these embodiments that generally gain the benefits provided by thermal processing of a drug deposited on a medical device in order to decrease the defect density and form a conformable drug coating. The above described embodiments should therefore not be considered limiting in regard to the following claims.

What is claimed is:

1. A method for applying a steroid coating to a medical device electrode, the method comprising the steps of:
   preparing a saturated solution comprising a steroid dissolved in an organic solvent;
   depositing the solution on a surface of the electrode driving off the organic solvent to form a coating having a crystalline structure on the electrode surface; and
   inducing micro-crack healing of the coating by heating the coating formed after the organic solvent has been substantially driven off.

2. The method of claim 1, further comprising the step of preparing the surface of the electrode to promote adhesion of the steroid prior to the depositing step.

3. The method of claim 1, further comprising the step of mixing the steroid with the organic solvent.

4. The method of claim 3, wherein the mixture is a saturated solution.

5. The method of claim 1, wherein the solvent comprises acetone.

6. The method of claim 1, wherein the solvent comprises methanol.

7. The method of claim 1, wherein the solvent comprises chloroform.

8. The method of claim 1, wherein the steroid is sparingly soluble in water.

9. The method of claim 8, wherein the steroid comprises beclomethasone diproprionate anhydrous.

10. The method of claim 1, wherein the steroid comprises dexamethasone.

11. The method of claim 1, wherein the coating is heated to a transition point resulting in a solid-state phase change of the coating.

12. The method of claim 1, wherein the coating is heated by directing a stream of hot air over the coating.

13. The method of claim 1, wherein the coating is heated by applying radio-frequency energy to the coating.

14. The method of claim 1, wherein the coating is heated by applying microwave energy to the coating.

15. The method of claim 11, wherein the steroid comprises beclomethasone diproprionate anhydrous and the coating is heated to a temperature between approximately 144 degrees Celsius and approximately 146 degrees Celsius.

16. The method of claim 3, wherein the depositing step comprises dipping the electrode into the mixture.

17. The method of claim 3, wherein the depositing step comprises dispensing the mixture of the steroid and the organic from a syringe.

18. The method of claim 12, further comprising the step of mounting the electrode on a fixture prior to the healing step and the healing step further comprises controlling the heating time by a motorized platform to which the fixture, on which the electrode is mounted, is coupled.

19. The method of claim 1, further comprising the step of assembling the medical device electrode into a lead.

20. A medical device prepared by the method of claim 1, comprising an electrode including a coating of steroid conforming to a surface of the electrode, the coating having a crystalline structure without micro-cracks.

21. The medical device of claim 20, further comprising an elongate lead body and wherein the electrode is a tip electrode terminating a distal end of the lead body.

22. The medical device of claim 21, wherein the tip electrode has a helical form.

23. The medical device of claim 21, wherein the tip electrode has a generally hemispherical form.

24. The medical device of claim 20, wherein the steroid comprises beclomethasone diproprionate anhydrous.

25. The medical device of claim 20, wherein the steroid comprises dexamethasone.

26. A method for applying a steroid coating to a medical device electrode, the method comprising the steps of:
   preparing a saturated solution comprising a steroid dissolved in an organic solvent;
   depositing the solution on a surface of the electrode driving off the organic solvent to form a coating having a crystalline structure on the electrode surface; and
   inducing micro-crack healing of the coating by heating the coating formed after the organic solvent has been substantially driven off, wherein
   heating occurs such that a solid-state phase change occurs but less than a degradation temperature of the steroid.

27. The method of claim 26, wherein heating occurs at about 145 degrees Celsius.

* * * * *